United States Patent [19]
Nojima et al.

[11] Patent Number: 5,169,781
[45] Date of Patent: Dec. 8, 1992

[54] CONTINUOUS PERFUSION APPARATUS UTILIZING AERATION

[75] Inventors: Youko Nojima; Hisatake Nojima, both of Kagoshima, Japan

[73] Assignee: Yuugen Kaisha Parasight, Chiba, Japan

[21] Appl. No.: 566,458

[22] PCT Filed: Feb. 22, 1989

[86] PCT No.: PCT/JP89/00180
§ 371 Date: Aug. 16, 1990
§ 102(e) Date: Aug. 16, 1990

[87] PCT Pub. No.: WO89/08141
PCT Pub. Date: Sep. 8, 1989

[30] Foreign Application Priority Data
Mar. 1, 1988 [JP] Japan .................. 63-49348

[51] Int. Cl.$^5$ .............................................. A01N 1/02
[52] U.S. Cl. ...................................... 435/283; 435/284; 417/118; 417/121; 261/119.1; 261/121.1
[58] Field of Search .............. 417/118, 121; 435/283, 435/284; 261/121.1, 119.1

[56] References Cited
U.S. PATENT DOCUMENTS

| | | | |
|---|---|---|---|
| 1,417,415 | 5/1922 | Sarlls | 417/118 |
| 3,116,347 | 10/1959 | Allen | 261/121.1 |
| 4,304,665 | 12/1981 | Hines | 261/121.1 |
| 4,450,118 | 5/1984 | Tuin | 261/121.1 |
| 4,704,074 | 11/1987 | McCullough | 417/118 |
| 4,970,143 | 11/1990 | Guidoux et al. | 435/283 |

FOREIGN PATENT DOCUMENTS
54-9004  1/1979  Japan .
63-173576 7/1988 Japan .

Primary Examiner—James C. Housel
Assistant Examiner—Maureen Wallenhorst
Attorney, Agent, or Firm—Jordan and Hamburg

[57] ABSTRACT

An apparatus for the continuous perfusion of a liquid in cell culture, hydroponic and breeding processes includes a container having a sealed lower portion and an open upper portion, a hollow tube having an upper end in the open upper portion and a lower end in the sealed lower portion of the container for introducing liquid to be perfused into the sealed lower portion, a blast pipe for introducing perfusing gas into the sealed lower portion of the container, and a hollow U-shaped pipe extending from above the sealed lower portion of the container and thereinto. The relative positioning of the ends of the hollow tube and hollow pipe at a particular height differential provides for a piston like movement of air and liquid to perfuse the liquid without requiring any electricity or motors.

4 Claims, 3 Drawing Sheets

CONTINUOUS PERFUSION APPARATUS UTILIZING AERATION

BACKGROUND OF THE INVENTION

Perfusion of a breeding liquid for breathing control and nutrition supply is essential for the breeding of life in processes such as cell culture, hydroponics and breeding. An apparatus for perfusing a liquid of small capacity is normally or usually such that water is moved by a water-flow pump to perfuse the liquid. For perfusion of a liquid of large capacity such as several hundred tons or several thousand tons, a super-huge water-flow pump is required in order to eliminate a stagnant area where the liquid is not perfused. Actually, a plurality of water-flow pumps are installed to cope with the stagnation, or the breeding liquid is completely replaced in order to cope with the stagnation. The present invention can cope with the automatic perfusion of the above-described liquid of small capacity only by simple aeration. It is considered that, in a principal aspect, the invention can cope with perfusion of a liquid of large capacity.

SUMMARY OF THE INVENTION

The present invention is originally directed to a perfusion apparatus, but, if a one-way valve is installed, the present invention functions as a water-flow pump. First, the background of a water-flow pump will be described. Mechanical construction of the normal or usual water-flow pump utilizes a driving force of a rotor which takes various configurations. Although it is possible to create a water-flow pump from a combination of piston movement and a one-way valve, utilization of an electric motor, which is superior in efficiency, does not so much create the water-flow pump of today. However, the apparatus of the present invention resembles a piston movement. That is, the present invention perfuses liquid upwardly and downwardly by water flow which utilizes the piston movement of air, and a valve is associated with the water flow to form a water-flow pump.

Regarding the perfusion apparatus, water is moved by the existing water-flow pump for the perfusion of the liquid of small capacity, to stir the liquid thereby eliminating the stagnant area, so that the liquid is perfused. In the present invention, since the liquid is moved upwardly and downwardly so as to be perfused, the liquid is perfused without any stagnant area. Appearance of a stagnant area is inevitable for a liquid of large capacity. The present invention solves the difficulty of perfusion by a simple construction.

An important aspect of the present invention is the function of a small pipe. That is, at one time, water enters a lumen and serves as a "water plug" so that air is accumulated. Subsequently, the water in the lumen is blown out to aerate the lumen so that the accumulated air is quickly opened and is removed.

BRIEF DESCRIPTION OF THE DRAWINGS

The invention will be better understood by reference to the accompanying drawings, in which.

DESCRIPTION OF THE PREFERRED EMBODIMENTS

Figure 1:
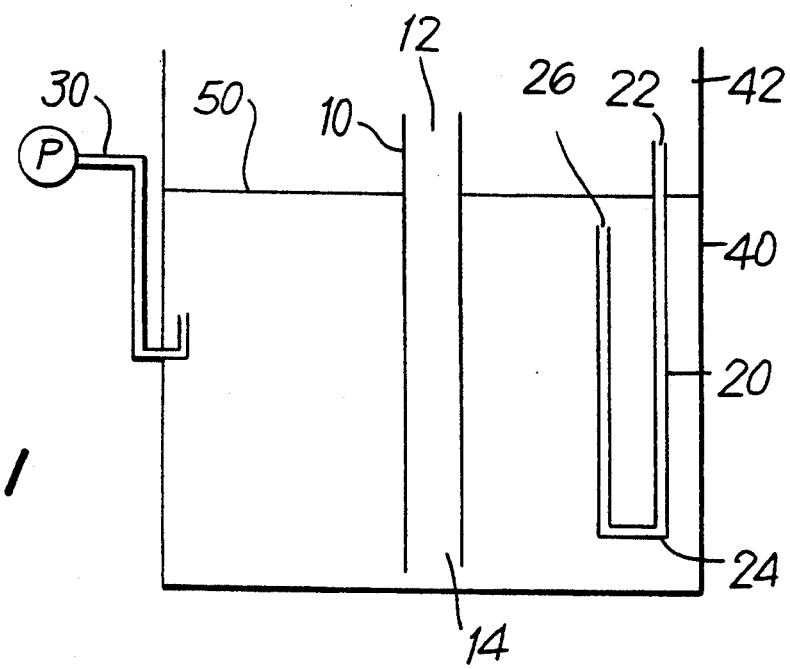
FIG. 1 is a vertical cross-sectional view of an empty perfusion apparatus according to the present invention.
Figure 2:
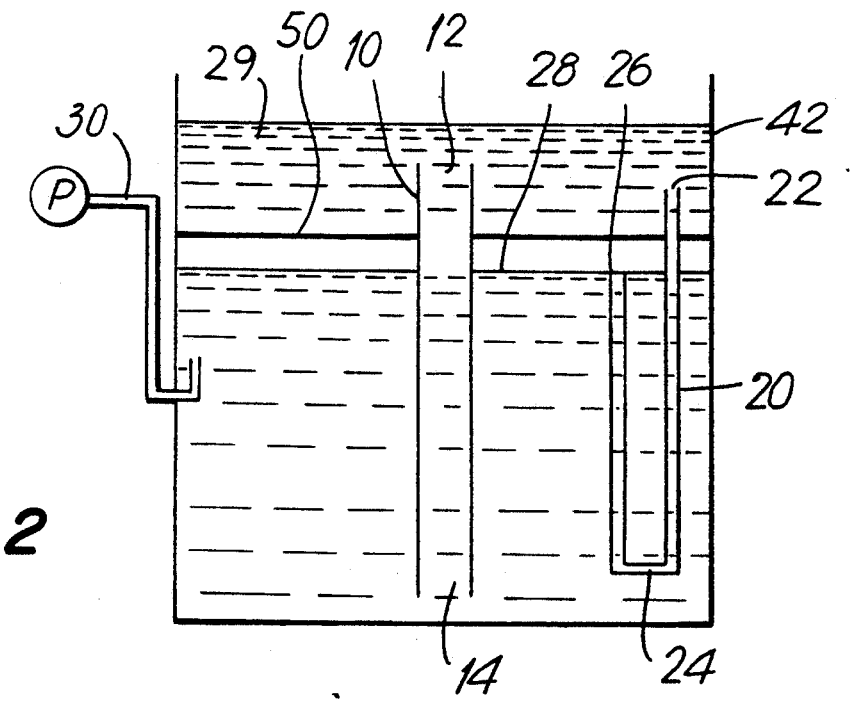
FIG. 2 is a vertical cross-sectional view of the perfusion apparatus of FIG. 1 filled with water to an artificial water level.

As shown commonly in FIGS. 1 through 5, the perfusion apparatus of the present invention includes a tube 10, a U-shaped small pipe 20 and a blast pipe 30, respectively. The water surface is indicated by the shaded areas. As commonly shown in FIGS. 1 through 4, the perfusion apparatus of the present invention further includes an uppermost end 12 and a lowermost end 14 of the tube 10, an uppermost end 22 of the right leg of the U-shaped small pipe 20 on the outside of a sealed container 40, a lowermost end 24 of the U-shaped small pipe 20 on the inside of the container 40 (also on the outside of the container 40 in FIG. 4), and an uppermost end 26 of the left leg of the U-shaped small pipe 20 on the inside of the container 40. The container 40 has an intermediate wall 50.

Figure 3:
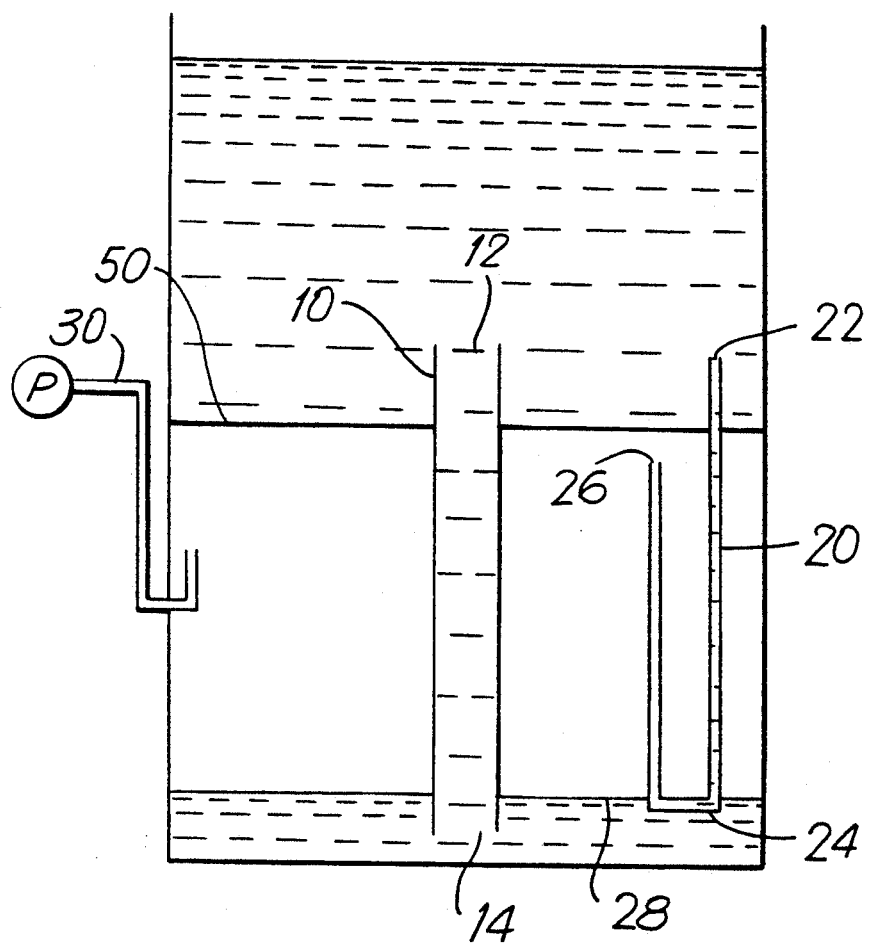
FIG. 3 is a vertical cross-sectional view of the perfusion apparatus of FIG. 2 after air has been charged thereinto.

FIG. 1 is a vertical cross-sectional view of an apparatus without water. If water is introduced without blowing of air under the condition illustrated in FIG. 1, the water enters the sealed container through the tube 10, and creates an artificial water surface 28 at the height of the uppermost end 26 of the left leg of U-shaped small pipe 20, while excess or surplus water 29 is accumulated in an upper outer portion 42 of sealed container 40. At this time, the condition is brought to one illustrated in FIG. 2. Subsequently, air blowing starts through the blast pipe 30, and the artificial water surface descends to the lowermost end 24 of the pipe 20. Simultaneously, the water surface within the left leg or U-shaped pipe 20 as shown in FIG. 3 also descends. In due course, the artificial water surface 28 (water surface within the pipe) further descends beyond 24. This is represented in FIG. 3. Now, where the pipe 20 is sufficiently thin in inner diameter, for example, of the order of 5 mm, the gravitational weight and the surface tension of the water act upon each other so that the water serving as the plug within the lumen of the pipe 20 is discharged, and the lumen of the pipe 20 is aerated. Thus, the air quickly escapes upwardly through the pipe 20. Outflow of the air is completed at the height of uppermost end 22 of small pipe 20. Then, again, the water flows backward in the pipe 20 through uppermost end 22 so that the lumen of the pipe 20 is plugged by the water. Thus, the communication of pipe 20 becomes interrupted. Since the air is blown continuously, the artificial water surface 28 again starts to descend. In this connection, if the pipe 20 has an inner diameter of the order of 40 mm, the surface tension of the water tends to be nullified by the gravitational weight of the water, so that the water is not discharged and the pipe 20 is not completely aerated. As a result, only a small quantity of delivered air ascends and the pipe 20 is not aerated. At this time, since the plug for the water cannot be released, there is no function of continuous perfusion.

The positions, where ends 22, 24, and 26 of the small pipe 20 are located, respectively, are very important. If end 22 is not sufficiently higher than end 26, there is the risk that the water does not flow backward very well. If end 22 and end 26 have a difference (water level difference) therebetween of the order of 1.5 cm, the water flows backward well. If the position of end 24 of the tube 10, and if there is no difference (water level difference), there is the possibility that air will pass through the tube 10. Ends 14 and 24 should have a height difference therebetween of more than the order of 1 cm.

Figure 4:
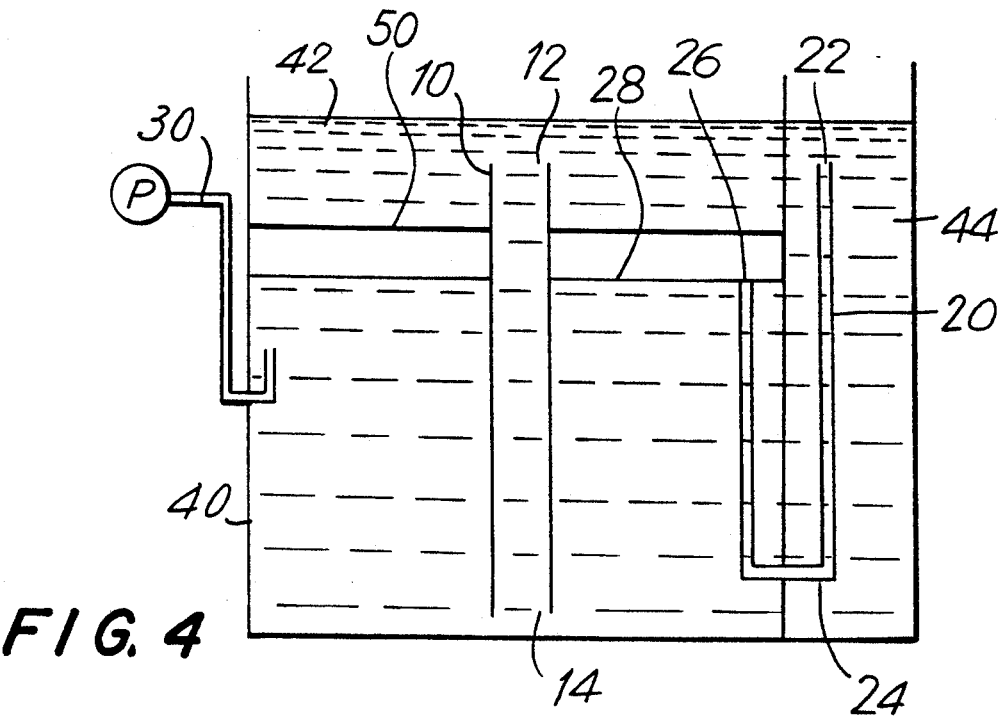
FIG. 4 is a vertical cross-sectional view of a second embodiment of a perfusion apparatus according to the present invention.

It is not necessarily required that the opening of the small pipe 20 be located in the upper portion 42 of the container 40. As shown in FIG. 4, if an adequate water level is given by another container 44 which is attached to the container 40, the apparatus has the requisite function of perfusion.

There is particularly no limit or restriction as to the position of the blast pipe 30 within the container. If the blast pipe 30 is installed at a lower position, there is a loss of energy. If the quantity of aeration is excessively large, the timing of backward flow of the water (water level of end 26) is lost. In this case, the inner diameter of the pipe 20 should be enlarged.

Figure 5:
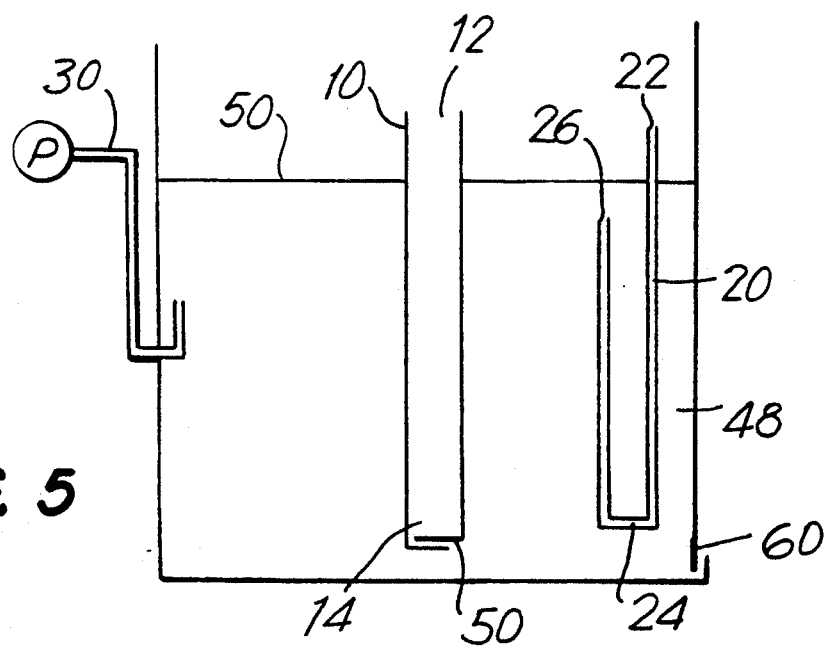
FIG. 5 is a vertical cross-sectional view of yet another embodiment of a perfusion apparatus according to the present invention.

In FIG. 5, 50 designates a valve which is mounted at the lowermost end 14 of the tube 10. The valve 50 is a one-way upward-only valve. A valve 60 is mounted on a side wall 48 which is located at a lower section of the container 40. The valve 60 is a one-way valve only in a direction toward the interior of the container 40. FIG. 5 is an apparatus according to the present invention which has the function of a pump.

The present invention is thus directed to such a perfusion arrangement that, when air is sent to a location within water, a course stagnating the air and a course opening the air are brought into a piston-like movement for the movement of water. The principle utilizes the fact that the liquid serves as a plug under the action of gravitational weight and surface tension, and the invention is directed to a perfusion apparatus created in addition to such a condition so as to release the duty of the plug.

It will be appreciated that the perfusion apparatus of the present invention provides perfusion utilizing rotation or involvement of the culture fluid in order to supply oxygen and nutrition in the culture of animal or plant cells. The perfusion apparatus according to the present invention provides a new and inexpensive perfusion method.

Further, if a one-way valve is mounted to regulate flow of the liquid in a constant direction, the perfusion apparatus functions as a water-flow pump. This means that air piping alone enables a simple and inexpensive pump to be installed which does not use electricity.

We claim:

1. An apparatus for the continuous perfusion of a liquid comprising a container having a side wall, a bottom wall, and an intermediate wall, said container having a closed lower container portion between said bottom wall and said intermediate wall, said container having an open upper container portion above said intermediate wall, a vertical tube extending through said intermediate wall, said tube having an upper end opening up into said upper container portion, said tube having a lower end opening into said lower container portion, a U-shaped pipe in said container having two legs extending upwardly from an interconnecting base which connects said two legs, said interconnecting base defining the lowermost portion of said U-shaped pipe, one of said legs having an upper end opening up into said lower container portion, the other of said legs having an upper end opening up into said upper container portion, said lower end of said tube being at a level lower than said interconnecting base of said U-shaped pipe, and blast pipe means for introducing perfusing gas into said lower container portion, whereby the perfusing gas introduced into said lower container portion by said blast pipe means forces the liquid in said lower container portion to flow from said lower container portion into said upper container potion via said tube until the level of the liquid in said lower container portion descends below the level of said interconnecting base, said U-shaped pipe containing liquid to function as a liquid plug as the liquid flows into said upper container portion from said lower container potion via said tube, the liquid in said U-shaped pipe being forced out of said U-shaped pipe by the perfusing gas when the level of liquid in said lower container portion descends below the level of said interconnecting base such that said U-shaped pipe no longer functions as a liquid plug and the perfusing gas then flows out of said U-shaped pipe to thereby allow the liquid in said upper container portion to flow into said lower container portion via said tube.

2. An apparatus according to claim 1, wherein said lower end of said tube is at a level more than 1 cm below the level of said interconnecting base of said U-shaped pipe.

3. An apparatus according to claim 1, wherein said U-shaped pipe has an inner diameter of about 5 mm.

4. An apparatus according to claim 1, wherein said upper end of said one leg of said U-shaped pipe which opens up into said lower container portion is about 1.5 cm lower than said upper end of said other leg of said U-shaped pipe.

* * * * *